United States Patent [19]

Secor et al.

[11] 4,163,855

[45] Aug. 7, 1979

[54] AZETIDINE COMPOUNDS AND PROCESS FOR PRODUCTION

[75] Inventors: Henry V. Secor, Midlothian; William B. Edwards, III, Richmond, both of Va.

[73] Assignee: Philip Morris Incorporated, New York, N.Y.

[21] Appl. No.: 889,147

[22] Filed: Mar. 23, 1978

Related U.S. Application Data

[62] Division of Ser. No. 590,646, Jun. 26, 1975, abandoned.

[51] Int. Cl.$^2$ .......................................... C07D 401/02
[52] U.S. Cl. ................................ 546/329; 260/239 A
[58] Field of Search ............. 760/296 R; 260/239 AR

[56] References Cited

PUBLICATIONS

Testa et al, Chem. Abstracts vol. 57, col. 15039 (1962).

Secor et al, Chem. Abstracts, vol. 86, abst. 120778g (1977).

Chem. Abstracts Subject Index. vol. 86, p. 4535CS (1977).

Klingsberg, Pyridine and Its Derivatives, Part One, pp. 2-3, Interscience Publishers, Inc. NY (1960).

Primary Examiner—John D. Randolph
Attorney, Agent, or Firm—Watson, Leavenworth, Kelton & Taggart

[57] ABSTRACT

Novel azetidine, and particularly 2-pyridyl-azetidine, compounds are disclosed. These compounds are produced from amino-esters by a sequence comprising conversion to the sulfonamide, reduction of the ester to the alcohol, sulfonation of the resultant alcohol and cylization to the N-sulfonylazetidine. This azetidine compound may then be transformed, as desired, to various N-derivatives by substitution of hydrogen or other univalent organic groups on the secondary amine of the azetidine ring.

4 Claims, No Drawings

AZETIDINE COMPOUNDS AND PROCESS FOR PRODUCTION

This is a division of application Ser. No. 590,646, filed June 26, 1975, now abandoned.

BACKGROUND OF THE INVENTION

Numerous azetidine compounds are known in the art and are credited with a spectrum of utilities. One such use derives from the relationship between azetidine and ethylenimine. The alkylating action evidenced by both of these compounds, and the effectiveness of the latter in various therapeutic schemes, has stimulated substantial investigation of azetidine analogs of ethylenimine derivatives of known clinical use for the control of neoplastic disease.

Azetidine compounds have also been successful as reagents in the well-known Vilsmeier-Haack reaction. There, it is azetidine amides which have been utilized.

The foregoing and other investigations have, however, been severely hampered by the low number of azetidine compounds available in the prior art. This scarcity is in turn dependent upon the prior art methods for producing such compounds. These methods permit the synthesis of relatively few azetidine compounds.

One such prior art method for producing azetidine compounds involves cyclization of amino-esters by treatment with a Grignard reagent to yield azetidinones ($\beta$-lactams) which may then be reduced with lithium aluminum hydride to yield the azetidine. This reaction has been successful, however, only where the amino-ester is limited in its substituents. Consequently it has not proven useful for the production of many desired compounds.

DESCRIPTION OF THE INVENTION

The present invention relates to a novel process for making azetidine compounds and to certain novel chemical compounds thereby produced. More particularly, this invention involves a process for transforming amino-esters into useful azetidine compounds, including novel 2-substituted-azetidine compounds.

The azetidine compounds of this invention are produced from $\beta$-amino-esters having the formula:

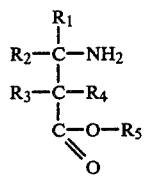

wherein:
each of $R_1$ and $R_2$ is hydrogen, alkyl, aryl, arylalkyl, heteroaromatic or alkylheteroaromatic; Each of $R_3$ and $R_4$ is hydrogen, alkyl, aryl, arylalkyl, heteroaromatic, or alkylheteroaromatic; and $R_5$ is alkyl, ordinarily methyl or ethyl.

As utilized here in description of the present invention, alkyl means an alkyl group of from 1 to 10, preferably 1 to 2 carbons. Aryl means an aromatic such as phenyl, tolyl, chlorophenyl or napthyl. Arylalkyl means a group such as benzyl. Heteroaromatic means pyridyl, furanyl and the like. By alkylheteroaromatics, it is meant the analogs of the arylalkyls such as picolyl.

In referring to aromatic ring configurations, substituents are not excluded. The degree of substitution permitted includes alkyl, cycloalkyl, aryl, arylalkyl, alkylheteroaromatic, heteroaromatic, and halogen at any of the available carbons of the ring. Acid addition salts of heteroaromatics and alkylheteroaromatics, such as the hydrochloride, are also included.

The scope of this invention is not restricted by the substituents on the amino ester. These substituents may, however, result in some retardation in the rate of the reactions for the production of azetidine compounds. Consequently, in a particularly preferred embodiment of the present invention, at least one of $R_3$ and $R_4$ is hydrogen. In a still more preferred embodiment, one of $R_1$ and $R_2$ is also hydrogen, the other being pyridyl or a substituted pyridyl.

These $\beta$-amino esters are readily available, although often only as salts due to the long term instability of the amino-esters themselves. Therefore, if the desired starting material is obtained as a salt, such as the hydrochloride, it should first be neutralized. This may be performed in conventional manner by, for example, treatment with an aqueous solution of sodium carbonate.

Alternatively, suitable $\beta$-amino-esters may be produced from the available, corresponding aldehydes, acids or alcohols. Thus the aldehyde may be converted to the acid as described in Castle et al, *J. Am. Pharm. Assoc.*, 43, 163 (1954) and then esterified. Similarly, the ester may be produced from a corresponding alcohol by oxidation followed by esterification.

In order to place the amino-esters in a form from which they can be cyclized into the azetidine ring structure, it is necessary first to convert both the ester and amine group into reactive form. This may be done by sulfonating each of these radicals, so as to produce the sulfonamide on the one hand and a sulfonate on the other. Suitable reagents for effecting this step are radicals having the formula: —SO$_2$R.

In this formula, R may be alkyl, aryl or arylalkyl. It is most preferred that the reagent be a tosyl radical, most preferably p-tosyl. Exemplary reagent compounds with which the amino-ester may be activated are the toluenesulfonyl halides such as p-tosyl chloride and p-tosyl bromide.

It has been discovered that the amino-esters of the present invention, particularly the $\beta$-substituted amino-esters, may not be converted directly into cyclicable form. A three-step sequence is therefore required.

First the sulfonamide is formed. This may be done, for example, by reaction of tosyl chloride with the amino-ester. This reaction should be performed in a suitable solvent, preferably a midly basic organic solvent such as pyridene. The sulfonamido-esters are produced at between 25° C. and the solvent freezing point, most preferably at −10° to +10° C., in at least about 1 to 2 hours. Thereafter, the sulfonamido-ester is reduced to produce the sulfonamide alcohol. This step may be performed utilizing any of the strong reducing agents known in the art. For example, a mixed metal hydride such as LiAlH$_4$ or NaAlH$_2$—(OCH$_2$CH$_2$OCH$_3$)$_2$ may be utilized. The reduced sulfonamide alcohol may then be reacted with more tosyl chloride, or the like, to produce the 3-sulfonamido-alkylsulfonate. This reaction should be performed as indicated for formation of the sulfonamido-ester, although up to about 24 hours may be required.

Cyclization is performed by cleavage of the sulfonate radical from the sulfonamide-alkylsulfonate. This cleavage, and the resultant cyclization may be performed by means known in the art. Exemplary of these means are the techniques set forth in Vaughan et al, *Journal of Organic Chemistry*, 26, 138 (1961). Most preferably, however, the cleavage and cyclization is performed utilizing potassium t-butoxide in a solution of t-butylalcohol. The product of this cyclization is the N-sulfonylazetidine, most preferably, p-toluenesulfonylazetidine.

This N-sulfonylazetidine may then in turn be reduced to produce corresponding N-hydrogen azetidine compounds (having substituents corresponding to those set forth hereinabove for the starting material $\beta$-aminoester). Any suitable reducing agent may be utilized for conversion of the N-sulfonylazetidine. Exemplary is sodium napthalenide. During treatment it is also desirable that a proton donor such as t-butanol be present to facilitate the conversion. Thus the combination of a suitable reducing agent and a proton donor provides a significantly increased yield of N-hydrogen azetidine compound. Again, low temperature is desirable, with from $-70°$ to $-40°$ C. being preferred. The reaction is virtually instantaneous.

In an additional embodiment, this azetidine may be alkylated to form the N-alkyl-azetidine. These compounds are similar in utility and may readily be produced by means known in the art. Thus, for example, N-methyl-azetidine compounds are produced in good yield by treatment of N-hydrogen azetidine with formaldehyde and formic acid in aqueous medium.

As set forth above, there are numerous utilities for the azetidine and substituted azetidine compounds of this invention. In addition, however, reference is made to U.S. Pat. Nos. 3,076,799 of Testa et al; 3,124,569 of Testa et al; and French Pat. No. 624,575 of Calanda-Stiftung. These indices of the prior art exemplify various of the specific uses to which these valuable products have been put.

As previously indicated, certain products of the present invention are also novel and not believed producible by means otherwise known in the art. These compounds comprise the 2-substituted, and particularly the 2-pyridyl, azetidines and derivatives thereof. These novel compounds have the formula:

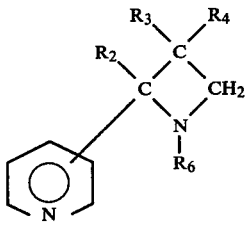

wherein:
  $R_2$, $R_3$, and $R_4$ are identically as set forth above with respect to the amino-ester precursors; and
  $R_6$ is hydrogen or alkyl, most preferably either hydrogen or methyl.

As indicated by the formula, the point of bonding between the pyridyl and azetidine groups is not critical. Ordinarily, however, the 3-pyridyl group is preferred. Also permissible, are substituents on the pyridyl group. Any of the four available valences may be satisfied by hydrogen, halogen, alkyl, aryl, arylalkyl, cycloalkyl, heteroaromatic, or alkyl heteroaromatic constituents. Further, this formula includes pyridyl or substituted pyridyl addition salts such as the hydrochloride.

These novel compounds have utilities similar to those of the azetidines in general and as already described. In addition, however, they have been discovered to be useful as pesticides. As such, they may be applied, ordinarily dissolved in a suitable solvent—for example, as a 1% aqueous solution—to plants infested with pests such as spider mites. It has been discovered that they are ordinarily useful not only against adult, but also nymph, form of such pests.

The present invention will be more apparent from the following. This exemplification is intended to illustrate this invention and is not limitative of its scope.

EXAMPLE 1

To a stirred suspension of 114 g (0.69 mole) of $\beta$-amino-$\beta$-(3-pyridyl)propionic acid in 2,850 ml of ethanol was added a 5° C. solution of 417 g of sulfuric acid in 240 ml of ethanol. After stirring for 1 hour, the resultant clear solution was left standing at room temperature for 48 hours and then concentrated to incipient crystallization in vacuum at a temperature below 50° C. The solution was added to a suspension of 715 g of sodium bicarbonate in 1430 ml of water over 1 hour. The temperature of the solution was maintained between 0° to 5° C. After stirring an additional 30 minutes, 300 ml of carbon tetrachloride was added and the admixture stirred for 10 minutes. The by-product salt was removed by filtration and the aqueous layer was extracted thoroughly with carbon tetrachloride. The combined organic extracts were dried and concentrated under vacuum to yield 87.11 g (65% yield) of crude ethyl $\beta$-amino-$\beta$-(3-pyridyl)propionate as a slightly viscous green liquid.

71 g (0.366 mole) of a solution of the propionate in 710 ml of pyridine was cooled to $-10°$ treated with 84 g (0.44 mole) of tosyl chloride. After standing in an ice bath for 2 hours and then overnight at room temperature, the solution was poured onto ice and diluted with 3 liters of water. The solid product was collected, washed with water, dried over potassium hydroxide to yield 90 g (70% yield) of ethyl $\beta$-(p-toluenesulfonamido)-$\beta$-(3-pyridyl)propionate.

89.7 g (0.26 mole) of the sulfonamide was added to a suspension of 12.7 g (0.34 mole) of lithium aluminum tetrahydride in 1250 ml of dry glyme. The mixture was stirred and heated under reflux for 1.5 hours. A saturated sodium chloride solution was added at a temperature of from 0° to 5° C. and the mixture stirred and heated under reflux for 30 additional minutes. The insolubles were removed by filtration after standing overnight and the cake was washed with 200 ml of boiling glyme followed by two 250 ml aliquots of ethyl alcohol. The pH was adjusted to 7.8 with sodium bicarbonate and hydrogen chloride. Most of the glyme and alcohol were removed under reduced pressure and the resulting solid collected, washed with water and dried in a desiccator to yield 75.6 g (95.5% yield) of 3-(p-toluenesulfonamido)-3-(3-pyridyl)propanol.

A solution of 70.5 g (0.23 mole) of the propanol in 750 ml of pyridine was cooled to $-5°$ C. 55 g (0.29 mole) tosyl chloride was slowly added to the solution, keeping the temperature below 5° C. The solution was then refrigerated for 24 hours at 4° C. and diluted with 4 liters of ice and water containing 24.4 g (0.29 mole) of sodium bicarbonate. The resultant crystalline solid was collected, washed with water and a small amount of ethanol and dried to yield 90.5 g (86% yield) of 3-(p- toluenesulfonamido)-3-(3-pyridyl)propyl p-toluenesulfonate.

2.88 g (0.074 mole) of clean potassium metal was then added to 2.7 liters of dry t-butanol. The mixture was stirred and heated for 90 minutes under reflux until the metal was dissolved. After adjusting the temperature to 30° C., 30 g (65.3 mmoles) of the sulfonate was added and the solution stirred and heated under reflux for 10 hours. The solution was filtered while hot and the cake washed with boiling $CH_2Cl_2$. The combined filtrate and washings were concentrated to dryness under reduced pressure to yield 2.6 g of crude solid which was then redissolved in $CH_2Cl_2$ and again filtered. The $CH_2Cl_2$ was displaced with boiling ethyl acetate and concentrated to 110 ml. After standing overnight, gleaming, dense, colorless prisms of 2-(3-pyridyl) p-toluenesulfonylazetidine were collected, 17.16 g (92% yield) of p-toluenesulfonylazetidine were collected. Concentration of the filtrate to 10 ml gave a second crop of the crystals.

Anal. Calcd.for $C_{15}H_{16}N_2SO_2$: C, 62.47; H, 5.59; $N_2$, 9.71; S, 11.12. Found: C, 62.66; H, 5.80; N, 9.90; S, 11.11.

EXAMPLE 2

A solution of sodium naphthalenide was prepared in 2 liters of dry glyme from 38.4 g (0.3 mole) of naphthalene and 5.75 g (0.25 mole) of sodium metal. This solution was added to 18.4 g (64 mmoles) of the azetidine of Example I dissolved in 4.72 g (64 mmoles) of t-butanol and 1 liter of glyme. 1,750 ml of the sodium naphthalenide solution was added over a 2-hour period keeping the temperature of the reaction medium between −60° and −65° C. 60 ml methanol was then added and the reaction mixture warmed to room temperature and left standing overnight. The solution was filtered, concentrated to a small volume under reduced pressure and the residue taken up in petroleum ether which was again filtered. The clear, off-colored petroleum ether filtrate was extracted with 5-20 ml aliquots of water and the combined water extracts concentrated under reduced pressure to 20 ml of a naphthalene-free solution of crude product. This solution was dried by azeotropic distillation using benzene and ethanol to give a benzene solution of product which, after removal of solvent, was distilled in vacuo to give one cut of clear, colorless 2-(3-pyridyl)azetidine (2.87 g or a 33.6% yield). This product exhibited a boiling point 73°-75° C./0.05 mm; ir (neat) 3225 (s), 800 (m), 713 cm$^{-1}$ (s); nmr (CDCl$_3$) δ 1.50 to 2.70 (m, 3) (which became 2H, with D$_2$O), 3.28 to 3.70, (m, 2) 4.87 (t, J=7H$_2$,1), 7.15 (m, 1), 7.72 (m, 1), 7.72 (m, 1), 7.72 (m, 1), 8.4–8.55 (m, 2); mass spectrum m/e (rel intensity) 134 (23, M+), 133 (31), 105 (100).

Anal. Calcd.for $C_8H_{10}N_2$: C, 71.61; H, 7.51; N, 20.88. Found: C, 71.69; H, 7.76; N, 21.01.

EXAMPLE 3

To a solution of 920 mg (6.88 mmoles) of the 2-(3-pyridyl)azetidine produced in Example 2 in 9 ml of water was added a solution of 660 mg (8.83 mmoles) of formaldehyde (40% w/w) in 9 ml of water and 755 mg (14.5 mmoles) of 88% formic acid in 9 ml of water. After heating on a steam bath for 2 hours, cooling to 0° C. and adding 1.21 g (14.4 mmoles) of sodium bicarbonate, the colored solution was concentrated under reduced pressure to 7 ml. It was then dried by azeotroping in benzene and ethyl alcohol to give a dry benzene solution containing insolubles. These insolubles were then filtered off to yield a solution of N-methyl-2-(3-pyridyl)azetidine.

Short path vacuum distillation gave 400 mg of N-methyl-2-(3-pyridyl)azetidine in the first fraction, b.p. 49°-50° C./0.025 mm; ir (neat) 3225 (s), 800 (m), 713 cm$^{-1}$ (s); nmr (CDCl$_3$) δ 1.9–2.5 (m, 2), 2.3 (s,3,CH$_3$), 2.9–3.4 (m,2), 3.9 (m,1), 7.25 (m,1), 7.78 (m,1) 8.3–8.6 (m,2); mass spectrum m/e (rel intensity) 148 (25, M+), 147 (28), 119 (100).

·Anal. Calcd. for $C_9H_{12}N_2$: C, 72.94; H, 8.16; N, 18.90. Found: 72.85; H, 8.07; N, 18.73.

We claim:

1. An azetidine compound having the formula

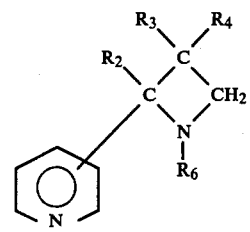

wherein:
R$_2$ is hydrogen or alkyl;
each of R$_3$ and R$_4$ are hydrogen or alkyl; and
R$_6$ is hydrogen or alkyl.

2. The azetidine compound of claim 1 wherein R$_6$ is hydrogen or methyl.

3. The azetidine compound of claim 2, wherein R$_2$ is hydrogen.

4. The azetidine of claim 1 in which the pyridyl radical is a 3-pyridyl group.

* * * * *

UNITED STATES PATENT AND TRADEMARK OFFICE
CERTIFICATE OF CORRECTION

PATENT NO. : 4,163,855

DATED : August 7, 1979

INVENTOR(S) : Henry V. Secor, William B. Edwards, III and Norman H. Cromwell

It is certified that error appears in the above-identified patent and that said Letters Patent are hereby corrected as shown below:

On the cover page the inventors are designated as "Henry V. Secor, Midlothian; William B. Edwards, III, Richmond, both of Va", but should be --Henry V. Secor, Midlothian; William B. Edwards, III, Richmond, both of Va.; Norman H. Cromwell, Lincoln, Nebr.--.

Signed and Sealed this

Twentieth Day of November 1979

[SEAL]

Attest:

RUTH C. MASON
Attesting Officer

LUTRELLE F. PARKER
Acting Commissioner of Patents and Trademarks